US011821827B2

(12) United States Patent
Cavazos Sepulveda

(10) Patent No.: US 11,821,827 B2
(45) Date of Patent: Nov. 21, 2023

(54) METHOD OF EVALUATING FOAMING AGENTS AND SURFACTANTS

(71) Applicant: SAUDI ARABIAN OIL COMPANY, Dhahran (SA)

(72) Inventor: Adrian Cesar Cavazos Sepulveda, Garcia (MX)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 271 days.

(21) Appl. No.: 17/334,333

(22) Filed: May 28, 2021

(65) Prior Publication Data

US 2022/0381665 A1 Dec. 1, 2022

(51) Int. Cl.
*G01N 13/02* (2006.01)
*G01N 1/38* (2006.01)
(Continued)

(52) U.S. Cl.
CPC .......... *G01N 13/02* (2013.01); *B01F 23/4111* (2022.01); *C09K 8/584* (2013.01); *G01N 1/38* (2013.01); *G01N 33/2823* (2013.01); *B01F 23/235* (2022.01); *B01F 23/4145* (2022.01); *G01N 2001/387* (2013.01); *G01N 2013/025* (2013.01); *G01N 2013/0275* (2013.01)

(58) Field of Classification Search
CPC ................ B01F 23/235; B01F 23/4111; B01F 23/4145; G01N 1/38; G01N 33/1833; G01N 33/2823
See application file for complete search history.

(56) References Cited

U.S. PATENT DOCUMENTS

| 4,589,276 A | 5/1986 | Djabbarah |
| 5,465,610 A | 11/1995 | Loisel |

(Continued)

FOREIGN PATENT DOCUMENTS

| DE | 3022848 A1 | 1/1982 |
| EP | 1416261 A2 | 5/2004 |
| WO | 2016/000739 A1 | 1/2016 |

OTHER PUBLICATIONS

International Search Report issued in PCT/US2022/031315, dated Aug. 12, 2022 (6 pages).

(Continued)

*Primary Examiner* — Kristina M Deherrera
*Assistant Examiner* — Jean F Morello
(74) *Attorney, Agent, or Firm* — Osha Bergman Watanabe & Burton LLP

(57) ABSTRACT

Methods of evaluating a surfactant may include ultrasonicating a mixture of oil, water, and the surfactant to form at least one of the following: a sub-macroemulsion, a macroemulsion phase or a combination of the aforementioned; separating the sub-macroemulsion from the macroemulsion phase; introducing the sub-macroemulsion into a foam container; performing a first automated phase identification of the sub-macroemulsion; introducing a gas into the sub-macroemulsion to generate a column of foam, where the column of foam has a height in the foam container; performing a second automated phase identification of the sub-macroemulsion; and measuring the height of the column of foam in the foam container. In these methods, the first and second automated phase identifications may be configured to quantify one or more liquid phases and a foam phase in the column.

16 Claims, 7 Drawing Sheets

(51) Int. Cl.
  *G01N 33/28* (2006.01)
  *B01F 23/411* (2022.01)
  *B01F 23/235* (2022.01)
  *B01F 23/41* (2022.01)
  *C09K 8/584* (2006.01)

(56) References Cited

U.S. PATENT DOCUMENTS

| | | |
|---|---|---|
| 5,597,950 A | 1/1997 | Mullen |
| 2002/0116137 A1 | 8/2002 | Kirts et al. |
| 2016/0287509 A1 | 10/2016 | Peffly et al. |
| 2017/0082528 A1 | 3/2017 | Li et al. |
| 2017/0119642 A1 | 5/2017 | Abel, Jr. et al. |
| 2018/0037809 A1 | 2/2018 | Frattarelli et al. |
| 2019/0112522 A1 | 4/2019 | Khamatnurova et al. |

OTHER PUBLICATIONS

Written Opinion of the International Searching Authority issued in PCT/US2022/031315, dated Aug. 12, 2022 (10 pages).

Nii, S. et al.: "Quantitative Approach to Ultrasonic Emulsion Separation"; Ulrasonics Sonochemistry; vol. 16, No. 1; Jan. 1, 2009, pp. 145-149 (5 pages).

Osei-Bonsu, Kofi, Nima Shokri, and Paul Grassia, "Foam stability in the presence and absence of hydrocarbons: From bubble-to bulk-scale", Colloids and Surfaces A: Physicochemical and Engineering Aspects 481, 2015, pp. 514-526 (13 pages).

Jafari, Seid Mahdi, Yinghe He, and Bhesh Bhandari, "Production of sub-micron emulsions by ultrasound and microfluidization techniques", Journal of Food Engineering 82.4, 2007, pp. 478-488 (11 pages).

Djenouhat, Meriem et al., "Ultrasonication-assisted preparation of water-in-oil emulsions and application to the removal of cationic dyes from water by emulsion liquid membrane: Part 2. Permeation and stripping", Separation and Purification Technology 63.1, 2008, pp. 231-238 (8 pages).

Belhaij, A et al., "Foamability and Foam Stability of Several Surfactants Solutions: The Role of Screening and Flooding", Journal of Petroleum & Environmental Biotechnology, vol. 6, Issue 4, 2015 (6 pages).

METHOD OF EVALUATING FOAMING AGENTS AND SURFACTANTS

BACKGROUND

Foaming agents and surfactants are used in various applications including in soap and detergent formulations as well as in the oilfield service industry in oil recovery processes. In particular, such foaming agents and surfactants may be used in oil recovery applications during injection processes for controlling gas mobility and mitigating the adverse effects of low gas viscosity, reservoir heterogeneity, and gravity override. In addition, foaming agents and surfactants have also been employed in near-wellbore production, matrix acidizing stimulation, hydraulic fracturing, gas shut-off, and water shut-off. The optimization of these processes requires a good understanding of the physical characteristics and properties of these foaming agents and surfactants as well as their behavior under reservoir conditions.

Methods for screening the behavior of foaming agents and surfactants in the presence of crude oil generally include diluting the foaming agents or surfactants in an aqueous solution followed by carefully placing the solution in the foam test tube so as to prevent bubble formation, and adding oil at the top or bottom of the aqueous solution. However, the immiscibility of the oil and water solutions instantaneously phase separates and air or nitrogen are then injected to the test tube and the foam is optically measured. Therefore, additional methods for screening foaming agents and surfactants are desirable.

SUMMARY

Certain embodiments of the disclosure will be described with reference to the accompanying drawings, where like reference numerals denote like elements. It should be understood, however, that the accompanying figures illustrate the various implementations described and are not meant to limit the scope of various technologies described.

In one aspect, embodiments disclosed herein are directed to methods of evaluating a surfactant. The methods may include ultrasonicating a mixture of oil, water, and the surfactant to form at least one of the following: a sub-macroemulsion, a macroemulsion phase or a combination of the aforementioned. The methods may further include separating the sub-macroemulsion from the macroemulsion phase; introducing the sub-macroemulsion into a foam container. The methods may further include performing a first automated phase identification of the sub-macroemulsion. The methods may further include introducing a gas into the sub-macroemulsion to generate a column of foam, where the column of foam has a height in the foam container. The methods may further include performing a second automated phase identification of the sub-macroemulsion; and measuring the height of the column of foam in the foam container. In these methods, the first and second automated phase identifications may be configured to quantify one or more liquid phases and a foam phase in the column.

Other aspects and advantages of this disclosure will be apparent from the following description made with reference to the accompanying drawings and the appended claims.

BRIEF DESCRIPTION OF DRAWINGS

FIG. 4A shows the emulsion after 1 minute after ultra-sonication. FIG. 4B shows the emulsion after 1 day after ultra-sonication. FIG. 4C shows the emulsion after 4 weeks after ultra-sonication.

DETAILED DESCRIPTION

Figure 1:
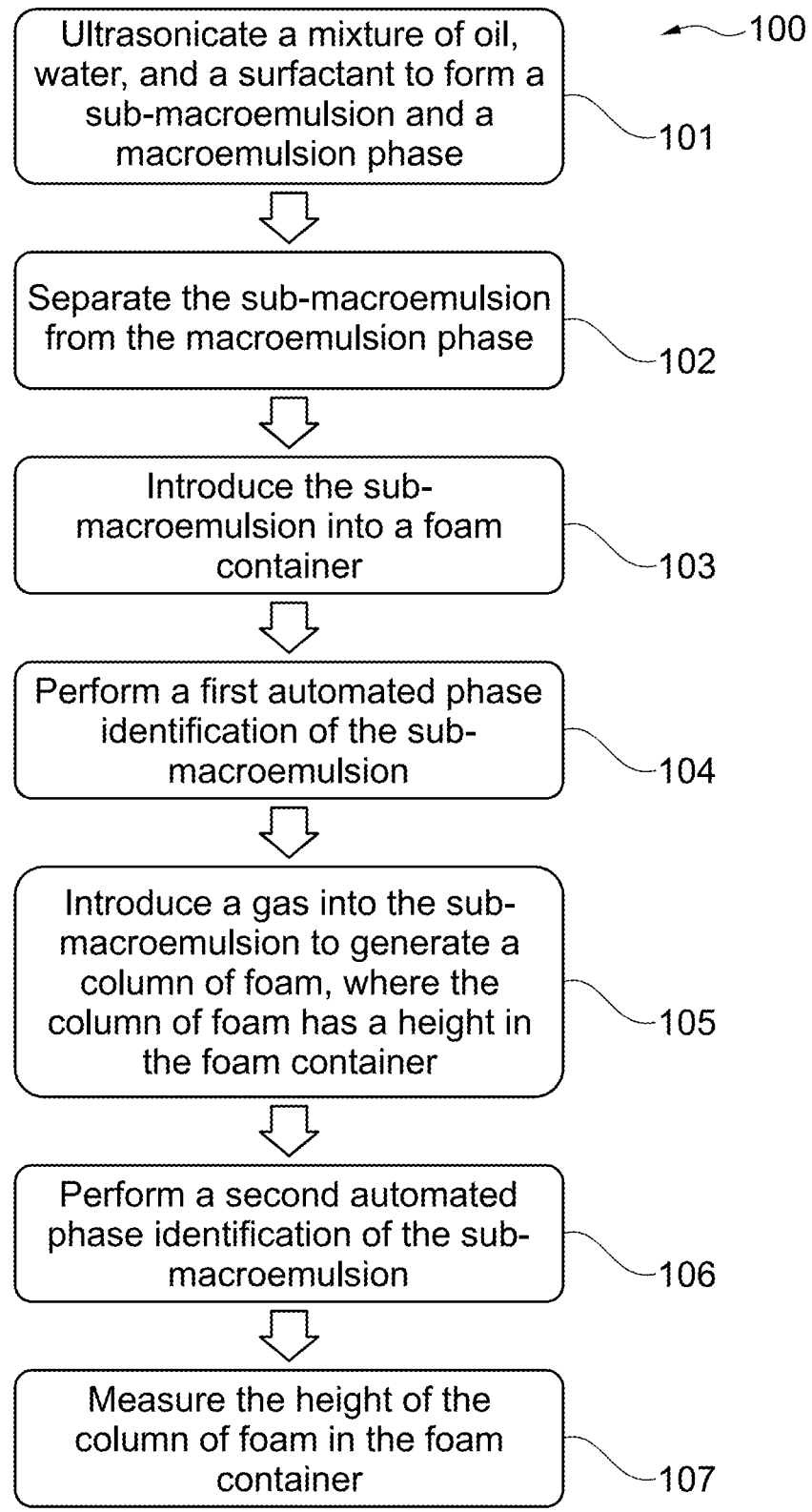
FIG. 1 is a flowchart describing a method in accordance with one or more embodiments.

Several technologies have been used to screen foaming agents and surfactants in terms of their foaming behavior and physical properties. For example, the Ross-Miles test may be used for screening the foamability of various solutions. In particular, in the Ross-Miles test, an increase in foam may be measured in three ways. First, the height of the foam is measured in millimeters after dropping the foaming agent or surfactant-containing solution drop by drop into a container from a determined height. Second, the density of the foam is measured by the number of foam cells per volume given. Third, the stability of the foam may also be measured using the Ross-Miles test and is expressed either in duration (in seconds) necessary for the foam to decrease by half of its initial volume or height of foam (in millimeters) after a given time. However, these techniques either do not employ reservoir conditions or use phase separated oil and aqueous solutions, which lead to inaccurate screening measurements.

Oil and water have different light absorption coefficients. A height determination test based on the principle that foam density affects the light absorption of a homogeneous solution may not be entirely accurate. Further, a monochromatic light absorption measurement, which is used in a Ross-Miles foam analyzer, may not properly distinguish the difference between light scattered by high-density foam or by oil droplets suspended in low-density foam. Therefore, to obtain accurate results using a light intensity-based foam test of a foaming agent or surfactant-containing solution in reservoir conditions, a solution with a macroscopically homogeneous optical density, or homogeneous opacity, is desirable.

Embodiments in accordance with the present disclosure relate to methods of evaluating foaming agents or surfactants in reservoir conditions based on measurements of solutions having homogeneous opacity. In some embodiments, the determination of the foamability of a foaming agent or a surfactant in the presence of oil maximizes the interfaces to increase the effects of their interactions. A method to quantify the number of interfaces in droplets in a given emulsion or phase separated solution uses the surface area to volume (S/V) ratio. Phase separated solutions obtained by traditional preparation methods method have a reduced number of interfaces. The S/V ratio of a sphere is inversely proportional to its radius according to Equation 1:

$$S/V = \frac{3}{r} \quad \text{Equation 1}$$

For example, comparing a phase separated solution having large droplets with a 1 millimeter (mm) radius (R) to a phase separated solution having the equivalent amount of components but with small droplets having a 0.5 mm radius (r), where R=2r, the difference in volume between a large droplet ($V_R$) and the volume of a small droplet ($V_r$), or number of small droplets in an equivalent volume of a large droplet, is given by Equation 2:

$$V_R = \frac{4\pi R^3}{3} = \frac{4\pi(2r)^3}{3} = 8*V_r \quad \text{Equation 2}$$

Similarly, the difference between the surface area of the large droplet and that of the small droplet is given by Equation 3:

$$A_R = 4\pi R^2 = 4\pi(2r)^2 = 4*4\pi r^2 = 4A_r \quad \text{Equation 3}$$

Thus, the ratio of surface area between a number of small droplets in an equivalent volume of a large droplet and that of a large droplet is given by Equation 4:

$$\sum A_r/A_R = \frac{8A_r}{4A_r} = 2 \quad \text{Equation 4}$$

Correspondingly, oil as droplets having 1 centimeter (cm) (10 mm) radius may have 10,000 less surface area and interactions than the same oil in the form of droplets having 1 micrometer (μm) (0.001 mm) radius. Consequently, the effects of a foaming agent or surfactant may be approximately 10,000 times stronger in solutions including droplets having 1 μm radii than in solutions including droplets having 1 cm radii.

In embodiments in accordance with the present disclosure, an ultra-sonication treatment may be performed to an oil and aqueous solution mixture before conducting a foaming test. The ultra-sonicated solution including oil, water, and a foaming agent or surfactant may form micron- and nanometer-sized emulsions. The interaction of the foaming agent or surfactant molecules with the oil may thus be enhanced, resulting in an increase in the duration of phase separation from seconds to days. This extended duration of stability may thus allow to perform emulsion foamability tests without the occurrence of decay or instabilities in the optical density or absorbance. Additionally, the ultra-sonicated solutions in some embodiments may become homogeneously opaque allowing more accurate optical measurements.

In some embodiments, the size of the droplets present in ultra-sonicated emulsions of oil, water, and foaming agent or surfactant mixtures may be of the same scale as the size of oil-field rock pores. For example, the droplet size may be in a range of from about 1 nm (nanometer) to about 1 μm, or from about 1 nm to about 500 nm, or from about 10 nm to about 400 nm, or from about 20 nm to about 350 nm, or from about 30 nm to about 300 nm. Accordingly, the size of the emulsion droplets may provide a behavior of the tested foaming agents or surfactants characteristic of that under reservoir conditions, in particular for surfactants and foaming agents in the presence of oil, such as crude oil, which may comprise hydrocarbons.

In some embodiments, methods in accordance with the present disclosure may provide a macroscopically homogeneous optical density or opacity for a light intensity-based foam test. In particular, the methods may use an ultra-sonication treatment performed to the oil and aqueous solution before conducting the foaming test. The ultra-sonicated solution contains oil, water, and foaming agents or surfactants and forms micron- and nanometer-sized emulsions. The interactions between the foaming agent and the oil are enhanced, resulting in delaying the phase separation and allowing the ultra-sonicated solution to have a stable and lasting optical density and absorbance providing an extended timeframe for the emulsion foamability test.

FIG. 1 is a flowchart that illustrates an embodiment method 100 of evaluating a foaming agent or surfactant. Referring to FIG. 1, in some embodiments, the method 100 may include ultrasonicating a mixture of oil, water, and a surfactant to form a sub-macroemulsion and a macroemulsion phase (block 101). In some embodiments, the method 100 may include separating the sub-macroemulsion from the macroemulsion phase (block 102). In some embodiments, the method 100 may include introducing the sub-macroemulsion into a foam container (block 103). In some embodiments, the method 100 may include introducing a gas into the sub-macroemulsion to generate a column of foam, where the column of foam has a height in the foam container (block 105). In some embodiments, the method 100 may include performing a first automated phase identification of the sub-macroemulsion before the introduction of gas (block 104) and a second automated phase identification of the sub-macroemulsion during the introduction of gas (block 106). In some embodiments, the method 100 may include measuring the height of the column of foam in the foam container (block 107).

Figure 2:
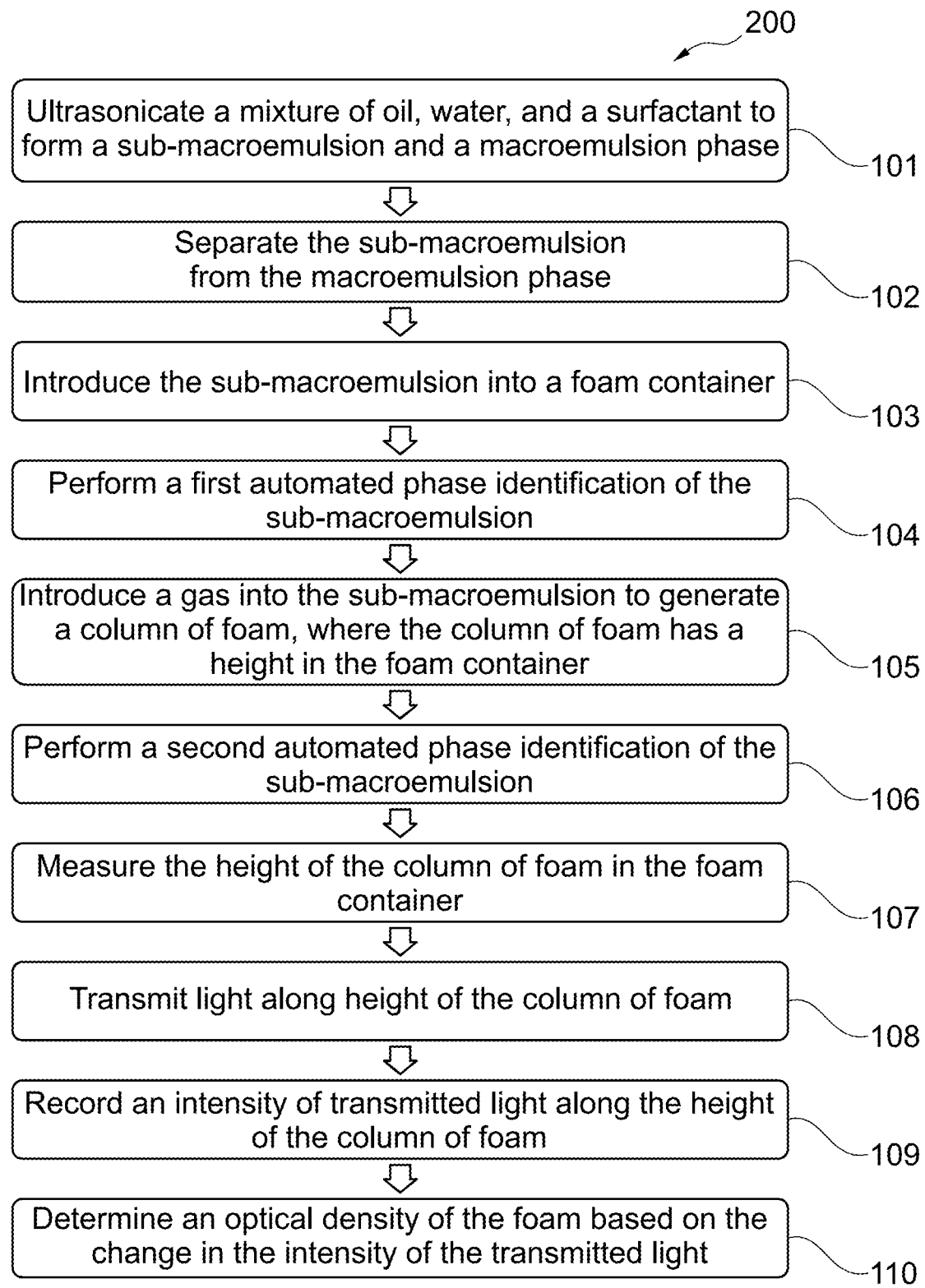
FIG. 2 is a flowchart describing a method in accordance with one or more embodiments.

FIG. 2 is a flowchart that illustrates an embodiment method 200 of evaluating a foaming agent or surfactant. Referring to FIG. 2, in some embodiments, the method 200 may include ultrasonicating a mixture of oil, water, and a surfactant to form a sub-macroemulsion and a macroemulsion phase (block 101). In some embodiments, the method 200 may include separating the sub-macroemulsion from the macroemulsion phase (block 102). In some embodiments, the method 200 may include introducing the sub-macroemulsion into a foam container (block 103). In some embodiments, the method 200 may include introducing a gas into the sub-macroemulsion to generate a column of foam, where the column of foam has a height in the foam container (block 105). In some embodiments, the method 100 may include performing a first automated phase identification of the sub-macroemulsion before the introduction of gas (block 104) and a second automated phase identification of the sub-macroemulsion during the introduction of gas (block 106). In some embodiments, the method 200 may further include measuring the height of the column of foam in the foam container (block 107). In some embodiments, the method 200 may further include transmitting light along height of the column of foam (block 108). In some embodiments, the method 200 may further include recording an intensity of transmitted light along the height of the column of foam (block 109). In some embodiments, the method 200 may further include determining an optical density of the foam based on the change in the intensity of the transmitted light (block 110).

In some embodiments, the methods of evaluating foaming agent or surfactant and their properties may include ultrasonicating a mixture of oil, water, and a surfactant at frequencies of about 20 kHz (kilohertz) to about 100 kHz, or about 20 kHz to about 80 kHz, about 30 kHz to about 60 kHz, about 40 kHz to about 50 kHz. The ultrasonication step may be carried out for at least 1 min (minute), or for about 1 min to about 60 min, or for about 5 min to about 50 min, or for about 10 min to about 45 min, or for about 15 min to about 40 min, or for about 20 min to about 35 min, or for about 25 min to about 30 min. The ultrasonication step may be carried out at temperature of about 0° C. to about 100° C., or of about 5° C. to about 90° C., of about 10° C. to about 80° C., of about 15° C. to about 50° C., of about 20° C. to about 40° C., of about 25° C. to about 35° C. The ultrasonication step may result in the formation of emulsion phases, which may include a macroemulsion phase and a sub-macroemulsion phase. The emulsions may include "water-in-oil" or "oil-in-water" emulsions depending on the ratio of the volume of liquid components in the mixture. The sub-macroemulsion phase may include droplets have sizes in a range of from about 1 nm to about 1 µm, or from about 1 nm to about 500 nm, or from about 10 nm to about 400 nm, or from about 20 nm to about 350 nm, or from about 30 nm to about 300 nm.

In one or more embodiments, the methods for may include an ultrasonication step that may be followed by the separation of the emulsion phases. The separation of the phases may include various physical separation processes based on gravity or coalescence properties of the emulsion phases. The sub-macroemulsion phase may then be introduced into a foam container, which may be a tube or column having a cylindrical cavity, where a foam column height measurement may be carried out. In the foam column, a strip light source may be mounted on a side of the foam column and a light detector may be placed on the opposite end of the foam column. A gas may be flowed through the column thus creating foam from the sub-macroemulsion solution. The gas may be one or a mixture of carbon dioxide, nitrogen, air, methane, ethane, propane, butane, hydrogen sulfide, flue or exhaust gas, or stream. More particularly, the gas may be carbon dioxide. In one or more embodiments, the ratio of solution volume to gas volume may be 1:10 to 10:1, 1:5 to 5:1, or 1:3 to 3:1. In one or more embodiments, the gas may be introduced into the solution at a constant rate, for example at a rate of from about 1 l/h to about 100 l/h (liter per hour), or from about 10 l/h to about 50 l/h and, or from about 20 l/h to about 40 l/h.

Figure 3A:
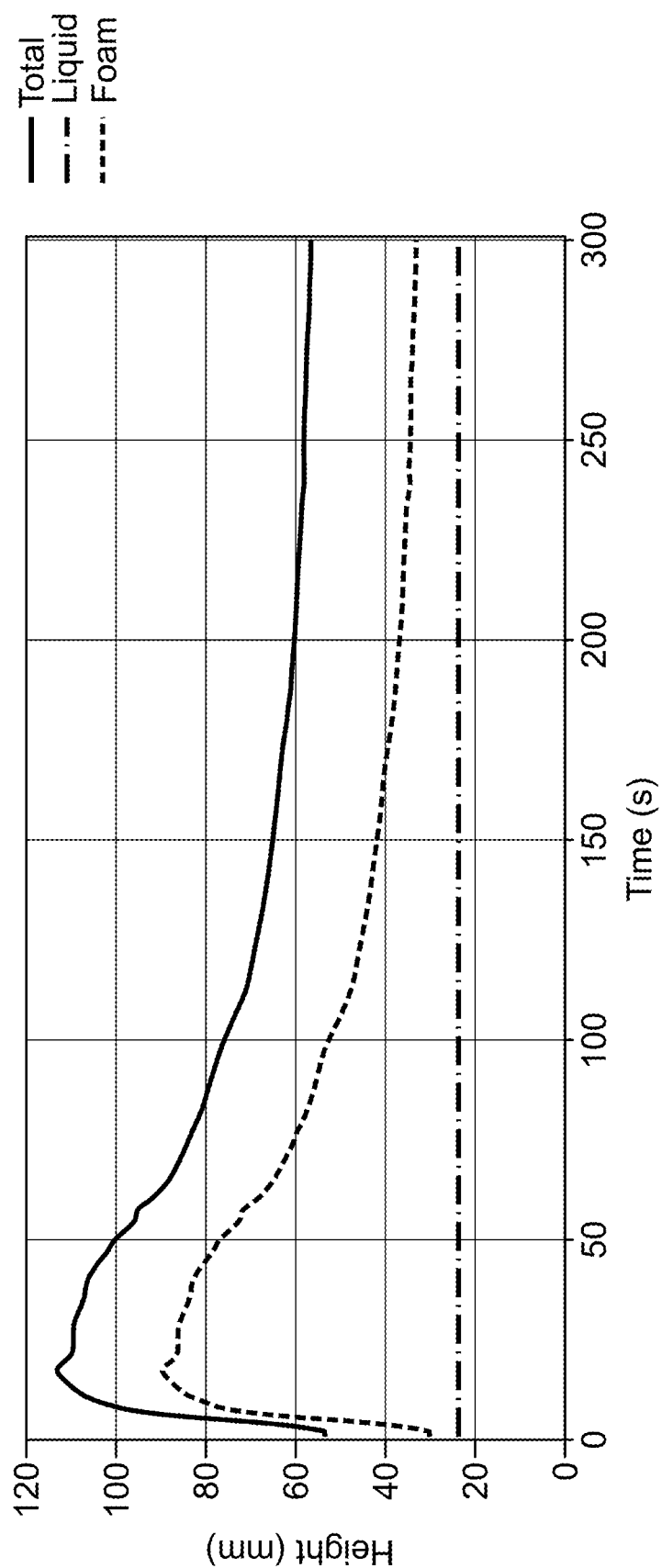
FIG. 3A-3B are graphs of the height of the liquid and foam phases in function of time from automated phase identification measurements in columns of foam obtained by methods with (FIG. 3A) and without (FIG. 3B) an ultra-sonication step.
Figure 3B:
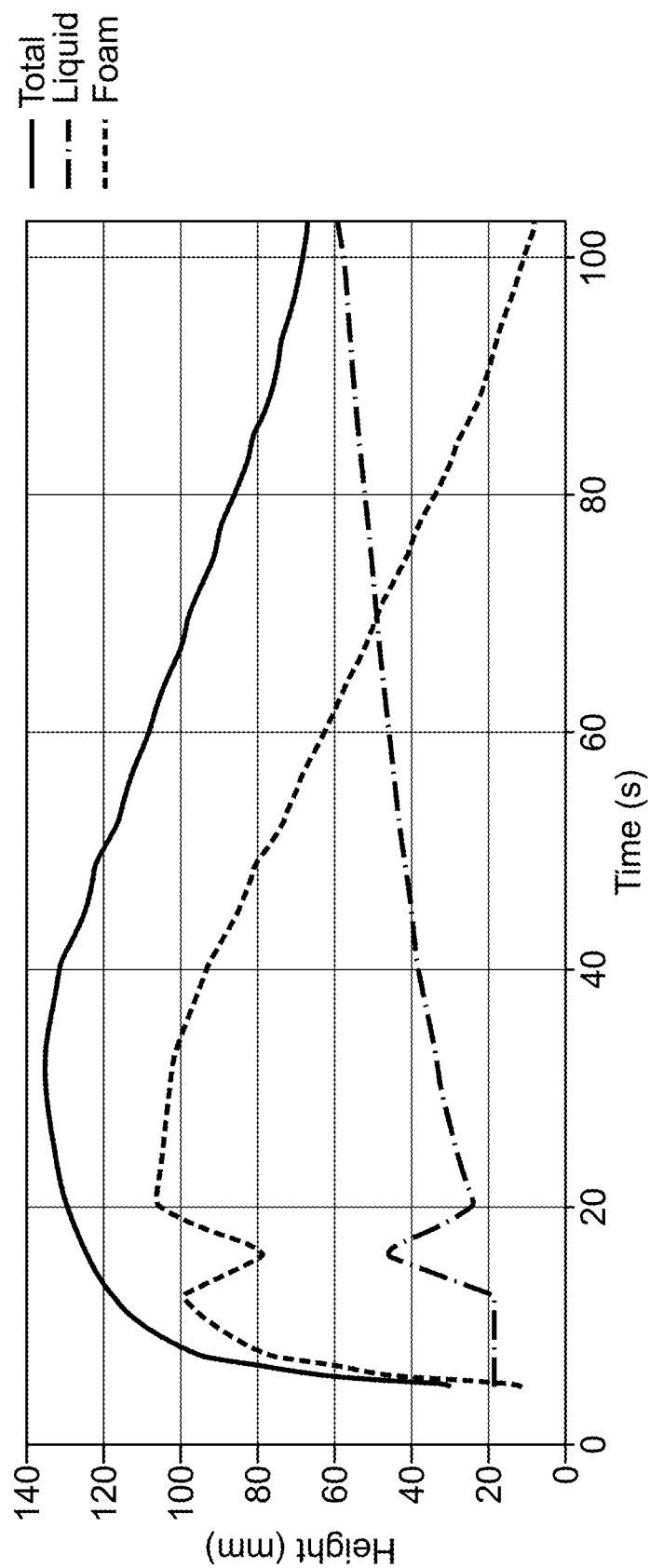

The foam height may be measured to characterize the foams, whereby physicochemical parameters of the foams can be derived from these measured quantities. In some embodiments, the methods may include measuring the height of the column of foam by using transmitted light along height of the column of foam. In one or more embodiments, the intensity of the light may be recorded along the height of the column during. The optical density, including transmittance and/or absorbance, may be determined based on the change on the intensity of the light before, during, and after foam generation. In one or more embodiments, the height of the foam column may be determined from the optical data based on the change in the intensity of the transmitted light. FIGS. 3A and 3B show graphs obtained from such optical data of the height of the liquid and foam phases in columns of foam in function of time for methods with and without an ultrasonication step, respectively.

In particular, ultrasonicated samples prepared according to the methods of one or more embodiments facilitate the automatic phase identification and differentiation between liquid and foam phases due to the optical density homogeneity of the totality of the liquid phases, which may include oil and/or water phases. This is in contrast with transparent liquid phases (such as water/brine) and opaque liquid phases (such as oil), for example, in a sample that is not ultrasonicated and oil floats on the top. In such a case, when the gas is introduced, the oil may splash onto the sides of the tube of the column and such splashed oil may be recognized as a change in the liquid height, as may be observed by the sudden peak of the liquid phase in the graph representing the liquid phase in a column of foam for methods without an ultrasonication step (FIG. 3B, liquid phase). This is an artificial peak in the identified liquid phase, since no liquid is added, and is wrongfully subtracted from the total foam height, leading to abnormal or erroneous foam height identification (the "dip" in the foam phase on FIG. 3B).

Thus, when a step of ultrasonication is carried out and an homogeneous sample is formed, such abnormal or erroneous foam height identification is avoided as shown in the graph obtained for a method including an ultrasonication step, where the liquid height remains stable and the graph illustrating the foam phase remains smooth, which resembles the single gas injection segment and the foam decay segment.

All types of foams, including metastable and non-stable foams, may be tested by these methods. The evaluation of foam stability may be carried out using the methods according to one or more embodiments. For example, the foam stability may be described by the time at which the foam height decreases when compared to the height of the foam after sonication and after introduction of the gas in the foam column. In addition, the foam stability may be described by the time at which the opacity of the totality of the liquid phases decreases. For example, the foam stability may be described by a change $\Delta h$ in the height h of the column of foam between a time when the foam is generated and a time of measurement of less than 1%, or less than 0.5%, or less than 0.1%. Additionally, the foam stability may be described by a change $\Delta O$ in the optical density of the totality of the liquid phases between a time when the foam is generated and a time of measurement of less than 1%, or less than 0.5%, or less than 0.1%. In one or more embodiments, the foam may maintain the same height and the opacity of the totality of the liquid phases may remain the same than the height and opacity after sonication for at least 1 minute, or at least 1 hour, or at least 10 hours, or at least 24 hours, or at least 100 hours.

The surfactant or foaming agent may comprise one or more foam-producing surfactants. The foaming agent can be an anionic, a nonionic, or an amphoteric surfactant with foam-producing characteristics. Anionic surfactants are those which ionize in aqueous solutions to form positively charged components, with the surface active portion being negatively charged. The surface active portion is typically a sulfate, sulfonate, carboxylate or phosphate. One class of anionic surfactants with strong foam-producing characteristics is the ammonium or sodium salts of ethoxylated sulfated alcohols, sometimes described as a salt of ethoxylate sulfate. In the methods according to one or more embodiments, the concentration of the surfactant in the mixture of surfactant, oil, and water, may be from about 0.01% w/v (weight per volume) to about 5% w/v, or from 0.1% w/v to about 2.5% w/v, or from 0.5% w/v to about 2% w/v.

Nonionic surfactants are those which have little or no tendency to ionize in aqueous solutions. The water soluble part of the molecule is attracted to water by means of a hydrogen bonding which is caused by the presence of atoms of a highly electronegative element such as oxygen. One class of nonionic surfactants, with strong foam-producing characteristics, is the linear alcohol ethoxylates which are the products of the reaction of a linear alcohol, such as decanol, with ethylene oxide. One example of this class is a nonylphenoxy poly(ethyleneoxy)ethanol.

Amphoteric surfactants are those whose molecules are characterized by two functional groups such as a positively charged amino group and a negatively charged carboxyl group. One class of amphoteric surfactants with strong foam-producing characteristics is the amido betaines. One example is cocoamidopropyl betaine.

Additionally, surfactant or foaming agent may comprise additives including ionic liquids and deep eutectic solvents, which can be hydrophilic, hydrophobic, and/or ampoteric/zwitterionic.

The foaming agent or surfactant may be selected for a particular reservoir brine because the foam-producing characteristics are influenced by the nature of reservoir rock, such as carbonate or sandstone, the properties of the reservoir, such as temperature and pressure, and composition of the reservoir fluids, such as salinity, divalent ion concentration, pH, etc. The water used in the aqueous solution may be fresh water, produced reservoir brine, or carbonated water.

According to one or more embodiments, when performing foam height experiments, the foaming agents or surfactants may exhibit an enhanced foamability, and a foam stability, as measured by the change in foam height and foam opacity, having an extended duration, allowing to perform reliable tests for surfactants and foaming agents in the presence of oil with increased accuracy.

EXAMPLE

The following example is merely illustrative and should not be interpreted as limiting the scope of the present disclosure.

A surfactant F18-32XL from Oil Chem Technologies Inc. in Sugarland TX was mixed with water. UTMN crude oil was then added to the resulting solution, and the mixture of 0.3 g of surfactant, 1.25 mL of crude oil, and 50 mL of water was ultrasonicated at about 40 kHz for 30 minutes at a temperature of about 25° C. The mixture formed a sub-macroemulsion containing micro- and nano-emulsions, which were separated from the remnant macroemulsion phases. The sub-macroemulsion was introduced in a foam column, where a height measurement was carried out. In the foam column, a strip light source was mounted on a side of the foam column and a light detector was placed on the opposite end of the foam column and a bubbler was placed on the underside of the foam column. Temperature was let to equilibrate and nitrogen gas was flowed through the bubbler to create foam from the micro/nano-emulsion solution. The intensity of the light was recorded along the height of the column during the whole experiment. The optical density (transmittance/absorbance) was determined based on the change on the intensity of the light before, during, and after foam generation, and the height of the foam column was inferred from these optical data.

Figure 4A:
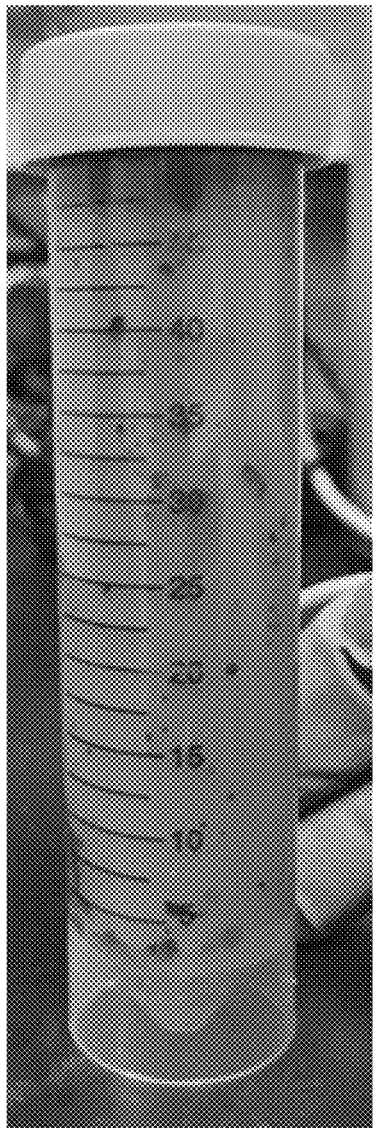
FIG. 4A-4C are photographs taken at different times of a test tube containing an ultra-sonicated emulsion of a crude oil, a foaming agent, and water according to Example 1.
Figure 4B:
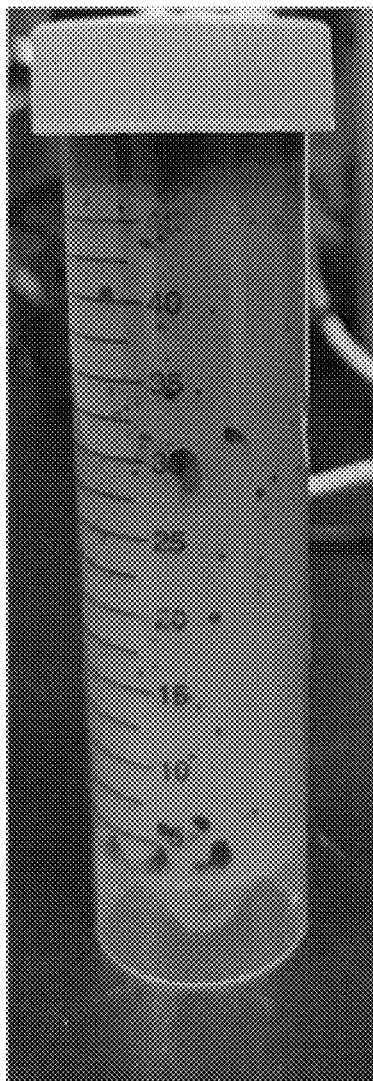
Figure 4C:
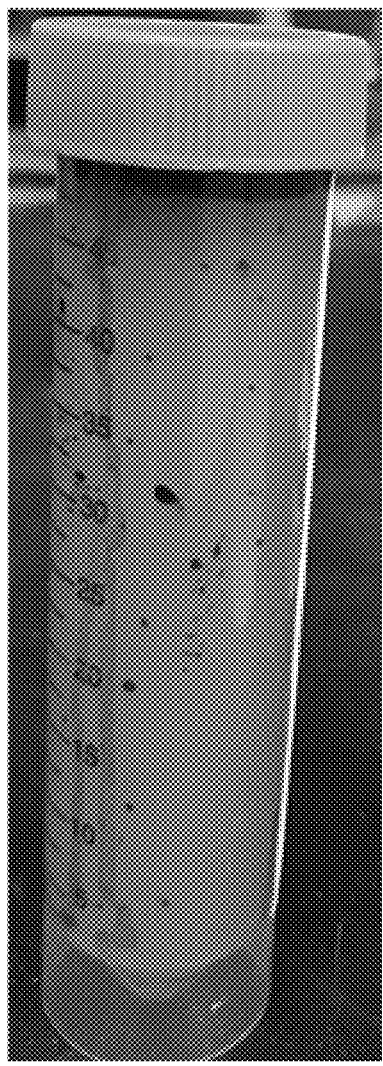

FIGS. 4A-4C show photographs taken of the sample in the foam column 1 minute after sonication (FIG. 4A), 1 day after sonication (FIG. 4B), and 4 weeks after sonication (FIG. 4C). As shown in FIGS. 4A-4C, the foam produced from a sub-macroemulsion obtained from an ultrasonicated mixture of surfactant, crude oil, and water, was stable it terms of foam height and liquid phase opacity for durations of at least 672 hours, which allows various measurements, without time pressure, providing reliability and accuracy of results using a light intensity-based foam test of the surfactant-containing solution under reservoir conditions.

While only a limited number of embodiments have been described, those skilled in the art having benefit of this disclosure will appreciate that other embodiments can be devised which do not depart from the scope of the disclosure.

Although the preceding description has been described here with reference to particular means, materials and embodiments, it is not intended to be limited to the particulars disclosed here; rather, it extends to all functionally equivalent structures, methods and uses, such as those within the scope of the appended claims.

The presently disclosed methods and compositions may suitably comprise, consist or consist essentially of the elements disclosed and may be practiced in the absence of an element not disclosed. For example, those skilled in the art can recognize that certain steps can be combined into a single step.

Unless defined otherwise, all technical and scientific terms used have the same meaning as commonly understood by one of ordinary skill in the art to which these systems, apparatuses, methods, processes and compositions belong.

The ranges of this disclosure may be expressed in the disclosure as from about one particular value, to about another particular value, or both. When such a range is expressed, it is to be understood that another embodiment is from the one particular value, to the other particular value, or both, along with all combinations within this range.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

The invention claimed is:

1. A method of evaluating a surfactant, comprising:
   a. ultrasonicating a mixture of oil, water, and the surfactant to form at least one of the following: a sub-macroemulsion, a macroemulsion phase or a combination of the aforementioned;
   b. separating the sub-macroemulsion from the macroemulsion phase;
   c. introducing the sub-macroemulsion into a foam container;
   d. performing a first automated phase identification of the sub-macroemulsion;
   e. introducing a gas into the sub-macroemulsion to generate a column of foam, where the column of foam has a height in the foam container;
   f. performing a second automated phase identification of the sub-macroemulsion;
   g. measuring the height of the column of foam in the foam container, where the first and second automated phase identifications are configured to quantify one or more liquid phases and a foam phase in the column; and h. determining a change in the height of the column of the foam after sonication and after introduction of the gas in the foam container.

2. The method of claim 1, where the mixture of oil, water, and the surfactant is ultrasonicated at frequencies of from about 20 kHz to about 100 kHz.

3. The method of claim 1, where the mixture of oil, water, and the surfactant is ultrasonicated for at least 1 minute.

4. The method of claim 1, where the mixture of oil, water, and the surfactant is ultrasonicated for a time of from about 1 minute to about 60 minutes.

5. The method of claim 1, where the mixture of oil, water, and the surfactant is ultrasonicated at a temperature of about 25° C.

6. The method of claim 1, where the step of measuring the height of the column of foam is performed by transmitting light through the column of foam.

7. The method of claim 1, further comprising:

f. transmitting light along height of the column of foam;

g. recording an intensity of transmitted light along the height of the column of foam, and h. determining an optical density of the totality of the liquid phases based on a change in the intensity of the transmitted light.

8. The method of claim 7, where a change $\Delta O$ in the optical density of the totality of the liquid phases between a time when the foam is generated and a time of measurement is less than 1%.

9. The method of claim 8, where the time of measurement is at least 1 minute from the time when the foam is generated.

10. The method of claim 1, where the oil comprises a crude oil.

11. The method of claim 1, where the oil comprises a hydrocarbon.

12. The method of claim 1, where the surfactant is selected from the group consisting of anionic, nonionic, and amphoteric surfactants.

13. The method of claim 1, where a concentration of the surfactant in the mixture, is from about 0.1% (w/v) to about 30% (w/v).

14. The method of claim 1, where the sub-macroemulsion comprises droplets having a size in a range of from about 1 nm to about 500 nm.

15. The method of claim 1, where the change in the height ($\Delta h$) of the column of foam between a time when the foam is generated and a time of measurement is less than 1%.

16. The method of claim 15, where the time of measurement is at least 1 minute from the time when the foam is generated.

* * * * *